United States Patent
Arba-Mosquera et al.

(10) Patent No.: US 12,023,280 B2
(45) Date of Patent: Jul. 2, 2024

(54) METHOD FOR CONTROLLING AN EYE SURGICAL LASER AND TREATMENT DEVICE

(71) Applicant: SCHWIND eye-tech-solutions GmbH, Kleinostheim (DE)

(72) Inventors: Samuel Arba-Mosquera, Aschaffenburg (DE); Rüdiger Werner, Biebergemünd-Bieber (DE); Nico Triefenbach, Mainaschaff (DE); Mario Shraiki, Stockstadt (DE)

(73) Assignee: SCHWIND eye-tech-solutions GMBH, Kleinostheim (DE)

( * ) Notice: Subject to any disclaimer, the term of this patent is extended or adjusted under 35 U.S.C. 154(b) by 0 days.

(21) Appl. No.: 16/995,272

(22) Filed: Aug. 17, 2020

(65) Prior Publication Data
US 2021/0052423 A1 Feb. 25, 2021

(30) Foreign Application Priority Data
Aug. 19, 2019 (DE) ............. 10 2019 122 167.6

(51) Int. Cl.
*A61F 9/008* (2006.01)
*A61B 17/00* (2006.01)

(52) U.S. Cl.
CPC ............... *A61F 9/00825* (2013.01); *A61B 2017/00154* (2013.01); *A61F 2009/00844* (2013.01);
(Continued)

(58) Field of Classification Search
CPC ........ A61F 9/00825; A61F 2009/00844; A61F 2009/00872; A61F 2009/00897; A61F 9/008; A61B 2017/00154; A61D 1/00
See application file for complete search history.

(56) References Cited

U.S. PATENT DOCUMENTS

| 7,351,241 B2 | 4/2008 | Bendett et al. |
| 2005/0165387 A1* | 7/2005 | Lubatschowski ... A61F 9/00825 606/107 |

(Continued)

FOREIGN PATENT DOCUMENTS

| EP | 1631223 B1 * | 7/2013 | ......... A61F 9/00827 |
| EP | 2 805 697 A1 | 11/2014 | |

(Continued)

OTHER PUBLICATIONS

Tinne et al (2014) Interaction Mechanisms of Cavitation Bubbles Induced by Spatially and Temporally Separated fs-Laser Pulses. PLoS One 9(12) (Year: 2014).*

(Continued)

*Primary Examiner* — Erin M Piateski
*Assistant Examiner* — Ranjani Mari Sundaresan
(74) *Attorney, Agent, or Firm* — MEDLER FERRO WOODHOUSE & MILLS PLLC (57) ABSTRACT

The invention relates to a method for controlling an eye surgical laser for the separation of a volume body with a predefined posterior interface and a predefined anterior interface from a cornea, comprising controlling the laser by means of a control device such that it emits pulsed laser pulses in a shot sequence in a predefined pattern into the cornea, wherein the interfaces of the volume body to be separated are defined by the predefined pattern and the interfaces are generated by means of an interaction of the individual laser pulses with the cornea by the generation of a plurality of cavitation bubbles generated by photodisruption, wherein the predefined pattern is generated by means of a mesh-like guidance of the emitted laser pulses and the control device controls the shot sequence of the laser such that a common overlap area of the cavitation bubbles is generated between adjacent cavitation bubbles. Further, the (Continued)

invention relates to a treatment device, to a computer program as well as to a computer-readable medium.

16 Claims, 2 Drawing Sheets

(52) U.S. Cl.
CPC ............... *A61F 2009/00872* (2013.01); *A61F 2009/00897* (2013.01)

(56) References Cited

U.S. PATENT DOCUMENTS

| | | | |
|---|---|---|---|
| 2015/0202084 A1* | 7/2015 | Schumacher | A61F 9/00825 606/5 |
| 2017/0087022 A1* | 3/2017 | Kurtz | A61F 9/008 |
| 2019/0015250 A1 | 1/2019 | Rathjen et al. | |

FOREIGN PATENT DOCUMENTS

| | | |
|---|---|---|
| EP | 2 865 362 A1 | 4/2015 |
| EP | 3 427 705 A1 | 1/2019 |

OTHER PUBLICATIONS

Kunert et al, Surface quality of human corneal lenticules after femtosecond laser surgery for myopia comparing different laser parameters, Graefes Arch Clin Exp Opthalmol (2011) 149: 1417-1424 (Year: 2011).*

First Examination Report issued in corresponding German Patent Application No. 10 2019 122 167.6 on Apr. 27, 2020.

* cited by examiner

METHOD FOR CONTROLLING AN EYE SURGICAL LASER AND TREATMENT DEVICE

FIELD

The invention relates to a method for controlling an eye surgical laser for the separation of a volume body with a predefined posterior interface and a predefined anterior interface from a human or animal cornea. Further, the invention relates to a treatment device with at least one surgical laser for the separation of a volume body with predefined interfaces of a human or animal eye by means of photodisruption and with at least one control device for the laser or lasers. Furthermore, the invention relates to a computer program as well as to a computer-readable medium.

BACKGROUND

Opacities and scars within the cornea, which can arise by inflammations, injuries or native diseases, impair the sight. In particular in case that these pathological and/or unnaturally altered areas of the cornea are located in the axis of vision of the eye, clear sight is considerably disturbed. In known manner, the thus altered areas are eliminated by so-called phototherapeutic keratectomy (PTK) by means of an ablatively effective laser, for example an excimer laser. However, this is only possible if the pathological and/or unnaturally altered areas of the cornea are located in the superficial layers of the cornea. Subjacent areas, in particular within the stroma, are not reachable by means of ablative laser methods. Here, additional measures such as for example the exposure of the subjacent areas have to be taken by means of an additional corneal incision. By the additional measures, the treatment duration is disadvantageously considerably increased. In addition, there is the risk that further complications such as for example the occurrence of inflammations at the incision locations occur by the additional corneal incisions.

BRIEF SUMMARY

Therefore, it is the object of the present invention to provide a method and a treatment device for controlling an eye surgical laser for the separation of a volume body with a predefined posterior interface and a predefined anterior interface from a human or animal cornea, by which the disadvantages of the prior art are overcome.

This object is solved by a method, a treatment device, a computer program as well as a computer-readable medium according to the independent claims. Advantageous configurations with convenient developments of the invention are specified in the respective dependent claims, wherein advantageous configurations of the method are to be regarded as advantageous configurations of the treatment device, of the computer program and of the computer-readable medium and vice versa.

An aspect of the invention relates to a method for controlling an eye surgical laser for the separation of a volume body with a predefined posterior interface and a predefined anterior interface from a human or animal cornea, wherein the method includes controlling the laser by means of a control device such that it emits pulsed laser pulses in a shot sequence in a predefined pattern into the cornea, wherein the interfaces of the volume body to be separated are defined by the predefined pattern and the interfaces are generated by means of an interaction of the individual laser pulses with the cornea by the generation of a plurality of cavitation bubbles generated by photodisruption, wherein the predefined pattern is generated by means of mesh-like guidance of the emitted laser pulses and the control device controls the shot sequence of the laser such that a common overlap area of the cavitation bubbles is generated between adjacent cavitation bubbles.

Thereby, it is allowed that the smoothness of the "incision" for generating the volume body can be improved. The smoothness can also be referred to as so-called "smoothness". In particular, the treatment duration can thereby be considerably shortened, possible complications by the usually required additional corneal incisions are avoided. Thus, the smoothness in particular indicates the smoother the volume body is generated, the cleaner incision surfaces and cleaner incision edges are generated at the volume body. Thus, the smoothness value in particular describes how clean the incision edges and the incision surfaces of the volume body are generated. In particular, it can for example be provided the smoother the incision is to be, the greater the preset smoothness value is to be selected.

In particular, the smoothness can for example be referred to as the absence of roughness. The roughness can for example be specified in units of length, for example micrometers. Presently, it can for example be provided that the roughness can be between nanometers and several micrometers. The smaller the roughness, the better the smoothness. The roughness can for example be calculated as a root mean square value of the deviations or as a standard deviation of a profile. It is also possible that the roughness can also be considered as an average value of the absolute deviations.

Thus, it is in particular provided that the common overlap area is generated between the adjacent cavitation bubbles independently of a respective geometry of a cavitation bubble in particular at least after the generated shot sequence. Thereby, bridges between the individual cavitation bubbles can in particular be prevented. Thus, the laser pulses are in particular emitted such that the common overlap area is generated between the cavitation bubbles at least after the shot sequence.

By the method according to the invention, it is then for example allowed to reliably remove pathological and/or unnaturally altered areas in the stroma of the cornea, that is in subjacent areas of the cornea, which is referred to as cornea. Basically, an additional exposure of the cornea by means of additional corneal incisions is not required.

In other words, it is in particular provided that the cavitation bubbles overlap and bridges do not arise between the cavitation bubbles, but the cavitation bubbles are as far apart from each other as a treatment can be faster performed and an unnecessary stress in the form of energy for the cornea is also prevented. By the overlap of the cavitation bubbles, thus, a confluent bubble with the preset smoothness or the preset smoothness value can be generated. Thereby, the volume body can be generated, which can then in turn be removed.

In addition, it can be provided that the laser is controlled such that at least one incision or at least one opening is generated in the cornea at a predefined angle and with a predefined geometry, wherein the incision or the opening intersects an interface of the volume body and is formed up to a surface of the cornea such that the volume body is removable from the cornea via the incision or the opening.

By the term "interfaces", it is also to be understood that the volume body can optionally be defined and separated by means of a single interface located in the cornea. By the method according to the invention, thus, phototherapeutic keratectomy methods can be performed in deep areas of the cornea, in particular of the cornea, in particular of the stroma, on the one hand. On the other hand, the treatment duration for the separation of the volume body is shortened, in addition, the energy input into the cornea of the patient is also significantly reduced.

Further preferably, it can be provided if the predefined pattern is defined based on one or more control datasets, wherein the control dataset or datasets include(s) control data for positioning and/or for focusing individual laser pulses in the cornea. The determination of the control datasets is known and they in particular result from for example topographic and/or tachymetric measurements of the cornea to be treated as well as the type, the position and the extent of the for example pathological and/or unnaturally altered area within the stroma of the cornea. In particular, the control datasets are generated at least by providing topographic and/or tachymetric and/or morphologic data of the untreated cornea and providing topographic and/or tachymetric and/or morphologic data of the pathological and/or unnaturally altered area to be removed within the cornea.

According to an advantageous form of configuration, the control of the laser is effected such that a mesh-like structure of the plurality of the cavitation bubbles is generated by means of the predefined pattern. Thus, a crisscross structure is in particular generated by the laser as the mesh-like structure. Thereby, a simplified variant for emitting the shot sequence is in particular realized. In particular by superimposing the cavitation bubbles, the crisscross pattern is thereby generated. Thus, depending on the mesh-like guidance, emission of the shot sequence is effected with a simple and coarse raster, wherein multiple cavitation bubbles are in particular thereby generated, which in particular have the common overlap area at least after the shot sequence such that the corresponding smoothness value can be complied with or generated. Thereby, it is allowed in simple yet reliable manner to generate the corresponding cavitation bubbles with the common overlap areas such that the smoothness value can be achieved.

In an advantageous form of configuration, the control of the laser is effected such that a lenticular volume body is separated. In other words, the volume body can therein be lenticularly formed, whereby a simple removal via the mentioned incision or the mentioned opening is possible. In that the volume body to be separated is only described and defined by the interfaces and these interfaces enclose for example the pathological and/or unnaturally altered tissue or the corresponding altered area on the one hand and are generated by means of photodisruption on the other hand, a full-surface or full-volume ablation of the volume body can be omitted. Only the interfaces are generated by means of photodisruption such that the predefined volume body can subsequently be removed from the cornea.

It is further advantageous if the control of the laser is effected such that the common overlap area is generated at least in time after the shot sequence. Thereby, it can be realized that the corresponding common overlap areas between the cavitation bubbles are formed at least after the shot sequence. In particular, it is thereby allowed at least after the shot sequence that the corresponding smoothness value is complied with or generated.

It is further advantageous if the control of the laser is effected such that a plurality of cavitation bubbles is generated along a cavitation bubble path of the predefined pattern. In other words, it is provided that a respective cavitation bubble is generated one after the other along a cavitation bubble path. Thereby, the predefined pattern is in particular generated. In other words, the generation of the cavitation bubbles is effected one after the other along the path. Thereby, the predefined pattern can be reliably generated.

In a further advantageous form of configuration, the control of the laser is effected such that a plurality of cavitation bubbles is generated along a plurality of cavitation bubble paths of the predefined pattern, wherein the overlap area is respectively generated between the respective cavitation bubble paths. Thus, it is in particular provided that the overlap area is respectively formed between the cavitation bubbles as well as between the individual cavitation bubble paths. Thereby, it is allowed that the volume body can be generated with the preset smoothness value. For example, with a preset distance of the cavitation bubbles, a consecutive cavitation bubble path can have a half distance laterally offset and be shifted parallel by root of three halves of the distance. Thus, it is allowed that the volume body can be generated with shortened treatment duration.

Further, it has proven advantageous if the control of the laser is effected such that a meandering cavitation bubble path or a spiral cavitation bubble path or a grid-like cavitation bubble path or an annular cavitation bubble path or a triangular cavitation bubble path or a helical cavitation bubble path is generated. Therein, the start of the photodisruption by the individual laser pulses can be effected in the center of the respective interface or also at the edge of the respective interface. Thereby, it is in particular allowed that different cavitation bubble paths can be generated by means of different shot sequences. Thus, the volume body can be highly flexibly generated.

In a further advantageous form of configuration, the control of the laser is effected such that the plurality of cavitation bubble paths for generating the predefined pattern at least partially overlap. In other words, it is in particular provided that at least the cavitation bubble paths overlap in crisscross manner after the shot sequence. Thereby, it is allowed that the corresponding overlap areas between the cavitation bubbles are generated at least after the shot sequence. Thereby, the lenticular volume body can be generated in simple yet reliable manner.

It is also advantageous if the control of the laser is effected such that for generating the predefined pattern, a first one of the cavitation bubble path of the plurality of cavitation bubble paths is generated in meandering or spiral or annular or grid-like or triangular or helical manner and at least a second cavitation bubble path of the plurality of cavitation bubble paths is generated different from the first cavitation bubble path in meandering or spiral or grid-like or annular or triangular or helical manner. In particular by the different generation of the cavitation bubble paths, it can be realized in particular after the shot sequence that they are located "crisscross" and thus can reliably form the interfaces. Thus, it is allowed in simple manner to generate the interfaces for the volume body.

It is also advantageous if the control of the laser is effected such that a number of cavitation bubble paths is generated depending on a preset smoothness value for the interfaces. In particular, the smoothness value can also be referred to as "smoothness". Thereby, the treatment duration can in particular be considerably shortened, possible complications by the usually required additional corneal incisions are avoided. In particular, the smoothness quasi describes a clean incision, in particular thus clean incision surfaces and clean incision edges. In particular for generating the smoothness, bridges between the cavitation bubbles are avoided.

In a further advantageous form of configuration, the control of the laser is effected such that at least a first cavitation bubble path of the plurality of cavitation bubble paths has a centering different from a second cavitation bubble path of the plurality of the cavitation bubble paths. In particular, it is allowed by the different centering of the cavitation bubble paths that the respective cavitation bubble paths overlap at least in certain areas. Furthermore, diffraction effects can be prevented from occurring after the treatment by the different centering.

It is further advantageous if the control of the laser is effected such that topographic and/or tachymetric and/or morphologic data of the cornea are taken into account. Thus, topographic and/or tachymetric measurements of the cornea to be treated as well as of the type, the position and the extent of the for example pathological and/or unnaturally altered area within the stroma of the cornea can in particular be taken into account. In particular, control datasets are generated at least by providing topographic and/or tachymetric and/or morphologic data of the untreated cornea and providing topographic and/or tachymetric and/or morphologic data of the pathological and/or unnaturally altered area to be removed within the cornea.

According to a further advantageous form of configuration, the control of the laser is effected such that the laser emits laser pulses in a wavelength range between 300 nanometers and 1400 nanometers, in particular between 700 nanometers and 1200 nanometers, at a respective pulse duration between 1 fs and 1 ns, in particular between 10 fs and 10 ps, and a repetition frequency of greater than 10 kHz, in particular between 100 kHz and 100 MHz. Such lasers are already used for photodisruptive methods in the eye surgery. The produced lenticule is subsequently removed via the incision in the cornea. However, the use of such photodisruptive lasers instead of ablatively acting lasers in the phototherapeutic keratectomy PTK is new and not known from the prior art. The use of photodisruptive lasers in the method according to the invention additionally has the advantage that the irradiation of the cornea is not to be effected in a wavelength range below 300 nm. This range is subsumed by the term "deep ultraviolet" in the laser technology. Thereby, it is advantageously avoided that an unintended damage to the cornea is effected by this very short-wavelength and high-energy beams. Photodisruptive lasers of the type used here usually input pulsed laser radiation with a pulse duration between 1 fs and 1 ns into the corneal tissue. Thereby, the power density of the respective laser pulse required for the optical breakthrough can be spatially narrowly limited such that a high incision accuracy in the generation of the interfaces is ensured.

A further aspect of the invention relates to a treatment device with at least one surgical laser for the separation of a volume body with predefined interfaces of a human or animal eye by means of photodisruption and with at least one control device for the laser or lasers, which is formed to execute the steps of the method according to the preceding aspect. The treatment device according to the invention allows that disadvantages occurring in the use of usual ablative treatment devices, namely relatively long treatment times and relatively high energy input by the laser into the cornea, are reliably avoided. These advantages are in particular achieved by the formation of the eye surgical laser as a photodisruptive laser.

Therein, the laser is suitable to emit laser pulses in a wavelength range between 300 nm and 1400 nm, preferably between 700 nm and 1200 nm, at a respective pulse duration between 1 fs and 1 ns, preferably between 10 fs and 10 ps, and a repetition frequency of greater than 10 kHz, preferably between 100 kHz and 100 MHz.

In an advantageous form of configuration of the treatment device, the treatment device comprises a storage device for at least temporary storage of at least one control dataset, wherein the control dataset or datasets include(s) control data for positioning and/or focusing individual laser pulses in the cornea, and includes at least one beam device for beam guidance and/or beam shaping and/or beam deflection and/or beam focusing of a laser beam of the laser. Therein, the mentioned control datasets are usually generated based on a measured topography and/or tachymetry and/or morphology of the cornea to be treated and the type of the pathologically and/or unnaturally altered area to be removed within the cornea.

Further features and the advantages thereof can be taken from the descriptions of the first inventive aspect, wherein advantageous configurations of each inventive aspect are to be regarded as advantageous configurations of the respectively other inventive aspect.

A third aspect of the invention relates to a computer program including instructions, which cause the treatment device according to the second inventive aspect to execute the method steps according to the first inventive aspect. A fourth aspect of the invention relates to a computer-readable medium, on which the computer program according to the third inventive aspect is stored. Further features and the advantages thereof can be taken from the descriptions of the first and the second inventive aspect, wherein advantageous configurations of each inventive aspect are to be regarded as advantageous configurations of the respectively other inventive aspect.

BRIEF DESCRIPTION OF THE FIGURES

Further features are apparent from the claims, the figures and the description of figures. The features and feature combinations mentioned above in the description as well as the features and feature combinations mentioned below in the description of figures and/or shown in the figures alone are usable not only in the respectively specified combination, but also in other combinations without departing from the scope of the invention. Thus, implementations are also to be considered as encompassed and disclosed by the invention, which are not explicitly shown in the figures and explained, but arise from and can be generated by separated feature combinations from the explained implementations. Implementations and feature combinations are also to be considered as disclosed, which thus do not comprise all of the features of an originally formulated independent claim. Moreover, implementations and feature combinations are to be considered as disclosed, in particular by the implementations set out above, which extend beyond or deviate from the feature combinations set out in the relations of the claims.

DETAILED DESCRIPTION

Figure 1:
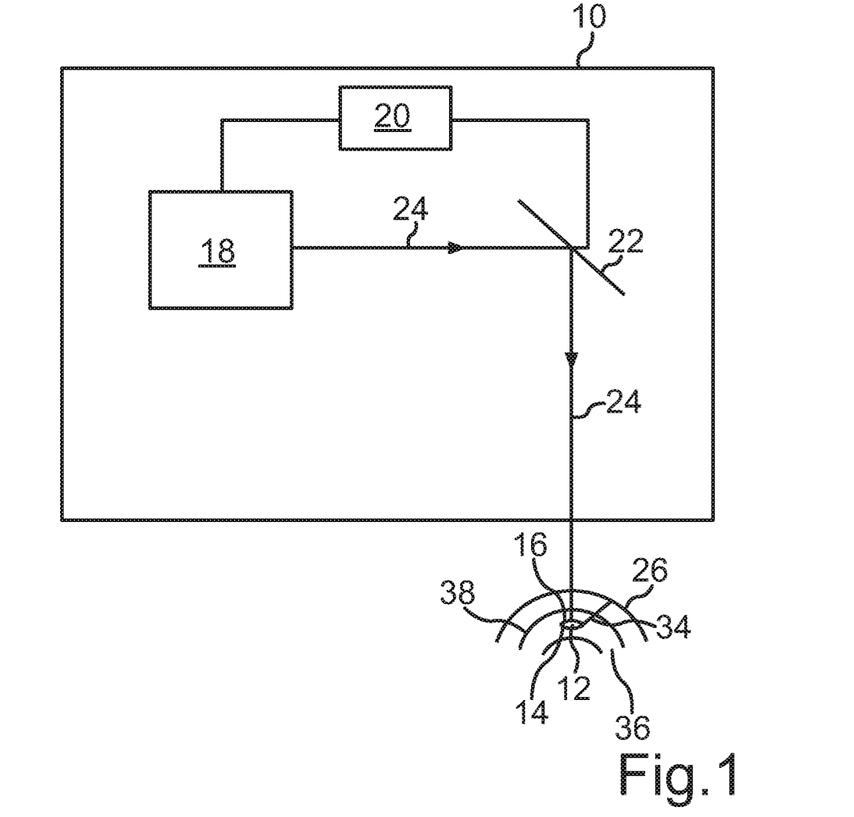
FIG. 1 is a schematic representation of a treatment device according to the invention.

FIG. 1 shows a schematic representation of a treatment device 10 with an eye surgical laser 18 for the separation of a predefined corneal volume or volume body 12 with predefined interfaces 14, 16 of a cornea of a human or animal eye by means of photodisruption. One recognizes that a control device 20 for the laser 18 is formed besides the laser 18, such that it emits pulsed laser pulses in a predefined pattern into the cornea, wherein the interfaces 14, 16 of the volume body 12 to be separated are generated by the predefined pattern by means of photodisruption. In the illustrated embodiment, the interfaces 14, 16 form a lenticular volume body 12, wherein the position of the volume body 12 is selected in this embodiment such that a pathological and/or unnaturally altered area 32 (see FIG. 2) within a stroma 36 of the cornea is enclosed. Furthermore, it is apparent from FIG. 1 that the so-called Bowman's membrane 38 is formed between the stroma 36 and an epithelium 28.

Furthermore, one recognizes that the laser beam 24 generated by the laser 18 is deflected towards a surface 26 of the cornea by means of a beam device 22, namely a beam deflection device such as for example a scanner. The beam deflection device 22 is also controlled by the control device 20 to generate the mentioned predefined pattern in the cornea.

The illustrated laser 18 is a photodisruptive laser, which is formed to emit laser pulses in a wavelength range between 300 nm and 1400 nm, preferably between 700 nm and 1200 nm, at a respective pulse duration between 1 fs and 1 ns, preferably between 10 fs and 10 ps, and a repetition frequency of greater than 10 KHz, preferably between 100 kHz and 100 MHz.

In addition, the control device 20 comprises a storage device (not illustrated) for at least temporary storage of at least one control dataset, wherein the control dataset or datasets include(s) control data for positioning and/or for focusing individual laser pulses in the cornea. The position data and/or focusing data of the individual laser pulses are generated based on a previously measured topography and/or pachymetry and/or the morphology of the cornea and the pathological and/or unnaturally altered area 32 for example to be removed within the stroma 36 of the eye.

Figure 2:
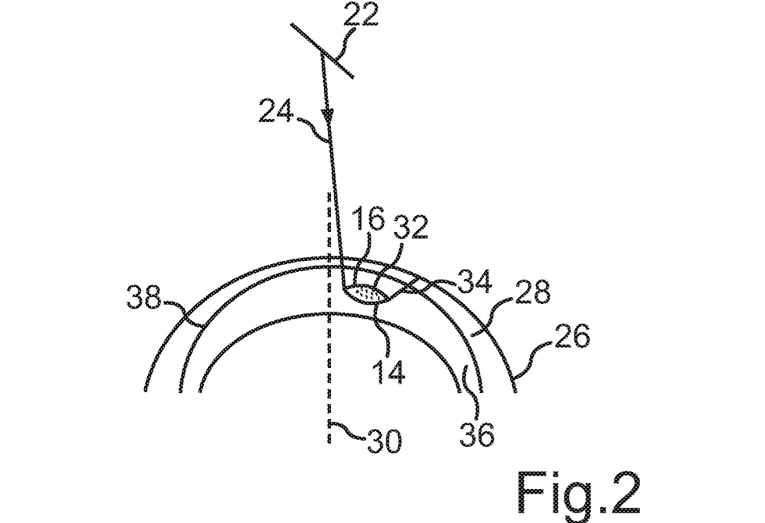
FIG. 2 is a schematic diagram of the generation of a volume body to be separated.

FIG. 2 shows a schematic diagram of the generation of the volume body 12 to be separated according to an embodiment of the present method. One recognizes that the interfaces 14, 16 are generated by means of the pulsed laser beam 24, which is directed towards the cornea or towards the surface 26 of the cornea via the beam deflection device 22. Therein, the interfaces 14, 16 form a lenticular volume body 12, which for example encloses the pathological and/or unnaturally altered area 22 within the stroma 36. Furthermore, the laser 18 generates a further incision 34 in the illustrated embodiment, which intersects the volume body 12 at a predefined angle and with a predefined geometry and is formed up to the surface 26 of the cornea. The volume body 12 defined by the interfaces 14, 16 can then be removed from the cornea via the incision 34. In the illustrated embodiment, the pathological and/or unnaturally altered area 32 is formed within the stroma 36 and outside of an optical axis 30 of the eye.

In the illustrated embodiment, the interface 14, that is the interface located deeper in the eye or the stroma 36, is first formed by means of the laser beam 24, wherein it then corresponds to the posterior interface 14. This can be effected by at least partially circularly and/or spirally guiding the laser beam 24 according to the predefined pattern. Subsequently, the interface 16 is generated in comparable manner, which then corresponds to the anterior interface 16 such that the interfaces 14, 16 form the lenticular volume body 12 (see also FIG. 1). Subsequently, the incision 34 is also generated by the laser 18. However, the order of the generation of the interfaces 14, 16 and of the incision 34 can also be changed.

Figure 3:
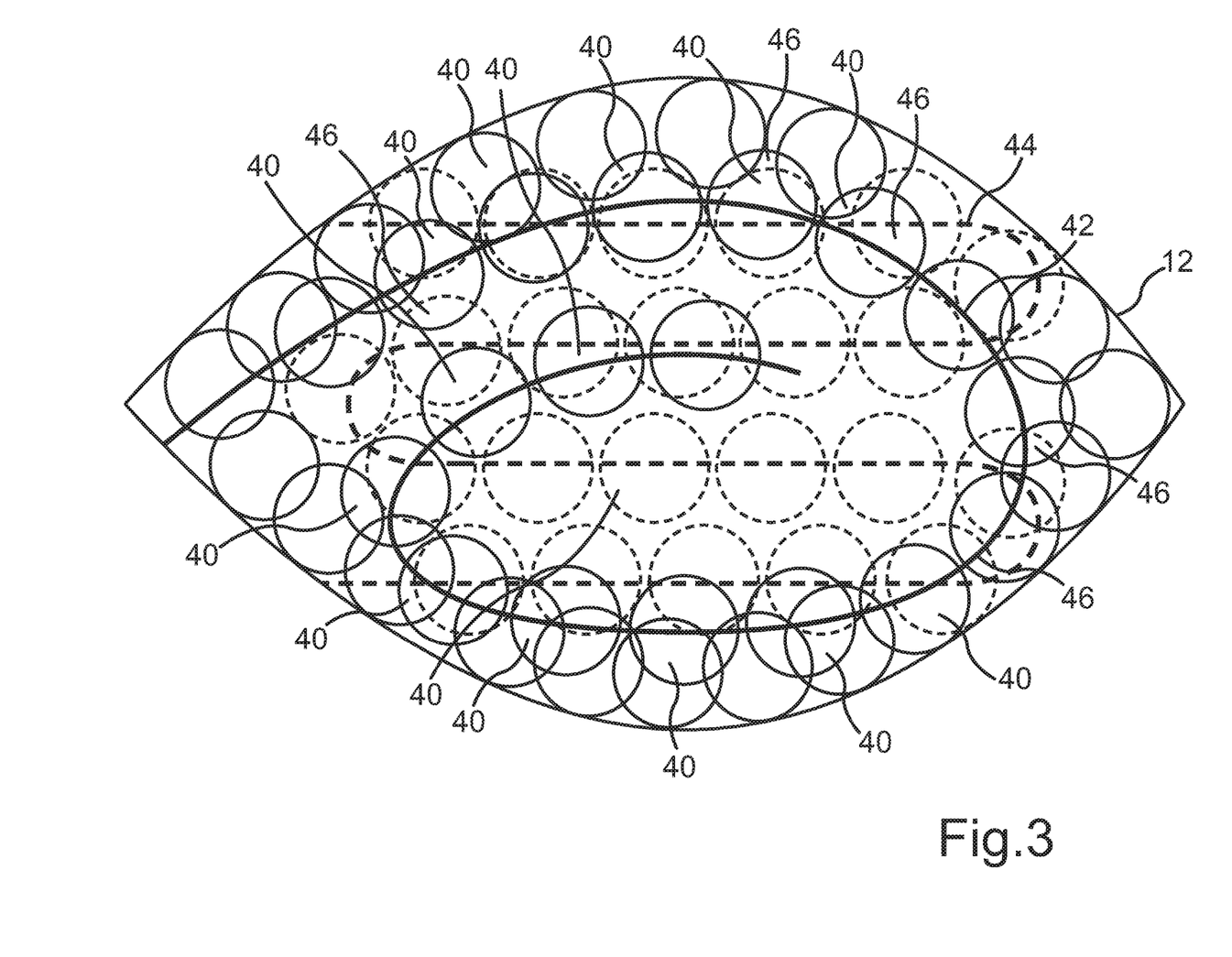
FIG. 3 is a schematic top view to a volume body.

FIG. 3 exemplarily shows a volume body 12 in a schematic top view. In particular, FIG. 3 shows that for controlling the laser 18 by means of the control device 20, the laser 18 is controlled such that it emits pulsed laser pulses in a shot sequence in a predefined pattern into the cornea, wherein the interfaces 14, 16 of the volume body 12 to be separated are defined by the predefined pattern and the interfaces 14, 16 are generated by means of an interaction of the individual laser pulses with the cornea by the generation of a plurality of cavitation bubbles 40 generated by photodisruption, wherein the predefined pattern is generated by means of a mesh-like guidance of the emitted laser pulses and the control device 20 controls the shot sequence of the laser 18 such that a common overlap area 46 of the cavitation bubbles 40 is generated between adjacent cavitation bubbles 40.

In particular, FIG. 3 shows that the control of the laser 18 is effected such that a mesh-like structure of the plurality of cavitation bubbles 40 is generated by means of the predefined pattern. Further, it is in particular provided that the control of the laser 18 is effected such that the common overlap area 46 is generated at least in time after the shot sequence. Furthermore, the FIG. 3 in particular shows that the control of the laser 18 is effected such that a plurality of cavitation bubbles 40 is generated along a cavitation bubble path 42, 44 of the predefined pattern. In the present embodiment, a plurality of the cavitation bubbles 40 is formed along a first cavitation bubble path 42. The first cavitation bubble path 42 is in particular spirally formed in this embodiment. Further, FIG. 3 shows that the cavitation bubbles 40 can be generated along a second cavitation bubble path 44. In the present embodiment, the second cavitation bubble path 44 is in particular formed meandering. In other words, FIG. 3 shows that the control of the laser 18 is effected such that the plurality of cavitation bubbles 40 is generated along the plurality of cavitation bubble paths 42, 44 of the predefined pattern, wherein the overlap area 46 is respectively generated between the respective cavitation bubble paths 42, 44. In particular, FIG. 3 further shows that the control of the laser 18 is effected such that a meandering cavitation bubble path 42, 44 or a spiral cavitation bubble path 42, 44 or an annular cavitation bubble path 42, 44 or a grid-like cavitation bubble path 42, 44 or a triangular cavitation bubble path 42, 44 or a helical cavitation bubble path 42, 44 is generated. The control of the laser 18 is further effected such that the plurality of cavitation bubble paths 42, 44 at least partially overlap for generating the predefined pattern. This is in particular also illustrated by the overlap area 46.

Further, it can in particular be provided that the control of the laser 18 is effected such that for generating the predefined pattern, the first cavitation bubble path 42 of the plurality of cavitation bubble paths 42, 44 is generated in meandering or spiral or annular or grid-like or triangular or helical manner and at least the second cavitation bubble path 44 of the plurality of cavitation bubble paths 42, 44 is formed different from the first cavitation bubble path 42 in meandering or spiral or grid-like or annular or triangular or helical manner.

In particular, it can further be provided that the control of the laser 18 is effected such that a number of cavitation bubble paths 42, 44 is generated depending on a preset smoothness value for the interfaces. In particular, the smoothness value can for example be generated by the number of cavitation bubble paths, wherein the smoothness value can for example be determined via the number n of the cavitation bubble paths as $n^{0.5}$.

Furthermore, it is seen in FIG. 3 that the control of the laser 18 is effected such that at least a first cavitation bubble path 42 of the plurality of cavitation bubble paths 42, 44 has a centering different from the second cavitation bubble path 44 of the plurality of cavitation bubble paths 42, 44.

FIG. 3 in particular only shows an intermediate step such that it can in particular be provided that for generating the preset smoothness and for generating the volume body 12, respectively, still further cavitation bubbles 40 not illustrated are generated. For the sake of clarity, FIG. 3 is correspondingly illustrated, but it is not to be regarded as exhaustive.

What is claimed is:

1. A method for controlling an eye surgical laser for separation of a volume body with a predefined posterior interface and a predefined anterior interface from a human or animal cornea, comprising:
    controlling the eye surgical laser by means of a control device such that the eye surgical laser emits pulsed laser pulses in a shot sequence in a predefined pattern into the human or animal cornea, wherein the predefined posterior interface and the predefined anterior interface of the volume body to be separated are defined by the predefined pattern;
    generating the predefined posterior interface and the predefined anterior interface by means of an interaction of the individual pulsed laser pulses with the human or animal cornea by generating a plurality of cavitation bubbles by photodisruption;
    generating the predefined pattern by means of a mesh-like guidance of the emitted pulsed laser pulses;
    controlling the shot sequence of the eye surgical laser by means of the control device such that a common overlap area of the cavitation bubbles is generated between adjacent cavitation bubbles;
    controlling the eye surgical laser by means of the control device such that the plurality of cavitation bubbles is generated along a plurality of cavitation bubble paths of the predefined pattern;
    sequentially generating the plurality of cavitation bubbles one after the other along each of the plurality of cavitation bubble paths;
    generating the common overlap area of the cavitation bubbles between respective cavitation bubble paths of the plurality of cavitation bubble paths;
    controlling the eye surgical laser by means of the control device such that a number of the plurality of cavitation bubble paths is generated depending on a preset smoothness value for the predefined posterior interface and the predefined anterior interface; and
    calculating a roughness as a root mean square value of the deviations or as a standard deviation of a profile or as an average value of absolute deviations, wherein smoothness is an absence of the roughness.

2. The method according to claim 1, wherein the control of the eye surgical laser is affected such that a mesh-like structure of plurality of cavitation bubbles is generated by means of the predefined pattern.

3. The method according to claim 1, wherein the control of the eye surgical laser is affected such that a lenticular volume body is separated.

4. The method according to claim 1, wherein the control of the eye surgical laser is affected such that the common overlap area of the cavitation bubbles is generated at least in time after the shot sequence.

5. The method according to claim 1, wherein the control of the eye surgical laser is affected such that one or more of the plurality of cavitation bubble paths generated is a meandering cavitation bubble path or a spiral cavitation bubble path or an annular cavitation bubble path or a grid-like cavitation bubble path or a triangular cavitation bubble path or a helical cavitation bubble path.

6. The method according to claim 1, wherein the control of the eye surgical laser is affected such that the plurality of cavitation bubble paths at least partially overlap for generating the predefined pattern.

7. The method according to claim 1, wherein the control of the eye surgical laser is effected such that for generating the predefined pattern, a first cavitation bubble path of the plurality of cavitation bubble paths is generated in a meandering or spiral or annular or grid-like or triangular or helical manner and at least a second cavitation bubble path of the plurality of cavitation bubble paths is generated in a manner different from the first cavitation bubble path.

8. The method according to claim 1, wherein the control of the eye surgical laser is affected such that at least a first cavitation bubble path of the plurality of cavitation bubble paths has a centering different from a second cavitation bubble path of the plurality of cavitation bubble paths.

9. The method according to claim 1, wherein the control of the eye surgical laser is affected such that topographic and/or pachymetric and/or morphologic data of the human or animal cornea are taken into account.

10. The method according to claim 1, wherein the control of the eye surgical laser is effected such that the eye surgical laser emits laser pulses in a wavelength range between 300 nm and 1400 nm, in particular between 700 nm and 1200 nm, at a respective pulse duration between 1 fs and 1 ns, in particular between 10 fs and 10 ps, and a repetition frequency of greater than 10 kHz, in particular between 100 kHz and 10 MHz.

11. A treatment device with at least one eye surgical laser for the separation of a volume body with predefined anterior and posterior interfaces of a human or animal cornea by means of photodisruption and with at least one control device, which is formed for controlling the at least one eye surgical laser according to the method of claim 1.

12. The treatment device according to claim 11, wherein the at least one control device comprises:
    at least one storage device for at least temporary storage of at least one control dataset, wherein the control dataset or datasets include(s) control data for positioning and/or for focusing individual pulsed laser pulses in the human or animal cornea; and
    at least one beam device for beam guidance and/or beam shaping and/or beam deflection and/or beam focusing of a laser beam of the eye surgical laser.

13. A non-transitory computer-readable medium having stored thereon a computer program, the computer program including instructions, which cause a treatment device with at least one eye surgical laser for the separation of a volume body with predefined interfaces of human or animal cornea by means of photodisruption and with at least one control device for controlling the at least one eye surgical laser to execute the method steps according to claim 1.

14. The method according to claim 1, wherein the control of the eye surgical laser is affected such that each of the plurality of cavitation bubble paths generated is one of a meandering cavitation bubble path or a spiral cavitation bubble path or an annular cavitation bubble path or a grid-like cavitation bubble path or a triangular cavitation bubble path or a helical cavitation bubble path.

15. The method according to claim 14, wherein the control of the eye surgical laser is affected such that the plurality of cavitation bubble paths at least partially overlap for generating the predefined pattern.

16. A method for controlling an eye surgical laser for separation of a volume body with a predefined posterior interface and a predefined anterior interface from a human or animal cornea, comprising:

controlling the eye surgical laser by means of a control device such that the eye surgical laser emits pulsed laser pulses in a shot sequence in a predefined pattern into the human or animal cornea, wherein the predefined posterior interface and the predefined anterior interface of the volume body to be separated are defined by the predefined pattern;

generating the predefined posterior interface and the predefined anterior interface by means of an interaction of the individual pulsed laser pulses with the human or animal cornea by generating of a plurality of cavitation bubbles by photodisruption;

generating the predefined pattern by means of a mesh-like guidance of the emitted pulsed laser pulses;

controlling the shot sequence of the eye surgical laser by means of the control device such that a common overlap area of the cavitation bubbles is generated between adjacent cavitation bubbles;

controlling the eye surgical laser by means of the control device such that a plurality of cavitation bubbles is generated along a cavitation bubble path of the predefined pattern; and sequentially generating the plurality of cavitation bubbles one after the other along the cavitation bubble path.

* * * * *

UNITED STATES PATENT AND TRADEMARK OFFICE
CERTIFICATE OF CORRECTION

PATENT NO. : 12,023,280 B2
APPLICATION NO. : 16/995272
DATED : July 2, 2024
INVENTOR(S) : Samuel Arba-Mosquera et al.

Page 1 of 1

It is certified that error appears in the above-identified patent and that said Letters Patent is hereby corrected as shown below:

In the Claims

Column 9, Line 58, "affected" should read --effected--.
Column 9, Line 62, "affected" should read --effected--.
Column 9, Line 65, "affected" should read --effected--.
Column 10, Line 2, "affected" should read --effected--.
Column 10, Line 9, "affected" should read --effected--.
Column 10, Line 21, "affected" should read --effected--.
Column 10, Line 26, "affected" should read --effected--.
Column 10, Line 62, "affected" should read --effected--.
Column 11, Line 2, "affected" should read --effected--.

Signed and Sealed this
Twenty-eighth Day of January, 2025

Coke Morgan Stewart
*Acting Director of the United States Patent and Trademark Office*